(12) United States Patent
Lewis et al.

(10) Patent No.: US 9,268,029 B2
(45) Date of Patent: Feb. 23, 2016

(54) EFFICIENT METHOD FOR RADIOCHROMIC FILM DOSIMETRY

(71) Applicant: ISP Investments Inc., Wilmington, DE (US)

(72) Inventors: David Fairhurst Lewis, Monroe, CT (US); Andre Micke, Chatham, NJ (US); Xiang Yu, Bridgewater, NJ (US)

(73) Assignee: ISP INVESTMENTS INC., Wilmington, DE (US)

( * ) Notice: Subject to any disclaimer, the term of this patent is extended or adjusted under 35 U.S.C. 154(b) by 0 days.

(21) Appl. No.: 14/385,051

(22) PCT Filed: Mar. 1, 2013

(86) PCT No.: PCT/US2013/028529
§ 371 (c)(1),
(2) Date: Sep. 12, 2014

(87) PCT Pub. No.: WO2013/138088
PCT Pub. Date: Sep. 19, 2013

(65) Prior Publication Data
US 2015/0041632 A1    Feb. 12, 2015

Related U.S. Application Data

(60) Provisional application No. 61/611,145, filed on Mar. 15, 2012.

(51) Int. Cl.
*G01D 18/00* (2006.01)
*G01T 1/08* (2006.01)
*G01T 1/02* (2006.01)
*G01T 7/00* (2006.01)
*A61N 5/10* (2006.01)

(52) U.S. Cl.
CPC ............... *G01T 1/08* (2013.01); *A61N 5/1048* (2013.01); *G01T 1/02* (2013.01); *G01T 7/005* (2013.01)

(58) Field of Classification Search
CPC .......... A61N 5/1071; G01T 1/02; G01T 1/20; G01T 1/08
USPC ...................................... 250/252.1
See application file for complete search history.

(56) References Cited

U.S. PATENT DOCUMENTS 6,285,031 B1    9/2001 Listl et al.
8,604,415 B2 *  12/2013 Micke et al. ............... 250/252.1
(Continued)

FOREIGN PATENT DOCUMENTS

WO    WO2011126725 A1    10/2011

OTHER PUBLICATIONS

International Search Report, PCT/US2013/028529 published on Sep. 19, 2013.

*Primary Examiner* — Kiho Kim
(74) *Attorney, Agent, or Firm* — William J. Davis

(57) ABSTRACT

The present invention provides a method for measuring a two-dimensional distribution of ionizing radiation doses with high spatial resolution. The method comprises exposing radiation sensitive film to a pattern of ionizing radiation to form a measurement film, exposing areas of radiation sensitive film to a plurality of known doses of the ionizing radiation to form a calibration film(s), scanning all the exposed films together with an unexposed radiation sensitive film at a single time to produce a digital image, measuring those areas of the digital image corresponding to the unexposed film and the calibration film(s) exposed to different known doses, associating the measured responses in the areas to the known doses and using the association to convert the values in the scanned image corresponding to the measurement film from scanner response values to dose values. In a preferred embodiment, all of the radiation sensitive films are the same type of film.

12 Claims, 9 Drawing Sheets

(56) References Cited

U.S. PATENT DOCUMENTS

| | | |
|---|---|---|
| 2006/0145091 A1 | 7/2006 | Patel |
| 2006/0159324 A1 | 7/2006 | Ritt et al. |
| 2007/0019790 A1 | 1/2007 | Lewis et al. |
| 2007/0114445 A1* | 5/2007 | Schell et al. ............... 250/474.1 |
| 2008/0089603 A1 | 4/2008 | Lewis et al. |
| 2008/0240364 A1* | 10/2008 | Main et al. .................... 378/207 |

* cited by examiner

EFFICIENT METHOD FOR RADIOCHROMIC FILM DOSIMETRY

BACKGROUND

The present invention relates to an efficient method for radiation sensitive film dosimetry, and in particular, to methods for measuring a distribution of ionizing radiation doses.

Radiotherapy has been used for years as a method for irradiating and selectively killing cancer cells while minimizing radiation exposure to adjacent tissue. The effectiveness of radiotherapy depends upon the absorbed dose or the amount of energy deposited within a tissue mass. Absorbed dose is typically measured in centigray or cGy units.

A radiation detection medium may be used to determine the amount and location of radiation to which a patient is subjected during radiation treatment. Particularly useful is a two-dimensional radiation detection medium that can determine radiation dose over an area. Examples are radiographic film, radiochromic film, phosphor plates, two-dimensional arrays of diodes or ion chambers and the like. The radiation detection medium typically has a response that varies systematically in accordance with the degree of radiation exposure. After exposure to ionizing radiation, radiation detection media such as radiographic and radiochromic films typically have a light transmission or optical density that varies systematically in proportion to the radiation dose. Calibration of the radiation sensitive film allows one to measure the absorbed dose indirectly by measuring the light transmission or optical density of the exposed radiation detection medium.

Radiochromic films are widely used by Medical Physicists to perform radiation dosimetry. Film is widely recognized as a "gold standard" for performing radiation dosimetry because of its exceptional spatial resolution, reaching to a level of at least 0.025 mm. Such high resolution is not possible with other measurement modalities including ion chambers, diodes and TLD. These other techniques are limited to spatial resolution in the range of 1 mm or coarser. Another advantage of radiochromic film is its tissue equivalence that the adsorbed radiation dose is truly reflection of the dose adsorbed by tissue.

Calibration curves for a radiation detection medium are often prepared by exposing one or more areas of the detection medium to different and known amounts of radiation using a linear accelerator or a similar device capable of generating a range of known dose levels. Another method frequently used is to expose the detection means to a continuously varying level of doses. This can be done by interposing a wedge of material with continuously varying thickness between the radiation source and the detection medium. Alternatively, the radiation sensitive medium may be sandwiched between two blocks and positioned so that the medium is in a plane parallel to the beam when it is exposed. In this configuration the dose applied to the radiation sensitive medium decreases continuously with depth below the top surface of the blocks. This type of exposure is often referred to as a depth-dose exposure. Typically, calibration curves are generated by measuring the response of the radiation sensitive medium for numerous different dose levels. In the instance of radiation films, it is common to measure the light transmission or optical density of the medium for numerous different radiation dosage levels.

Until now, a disadvantage of dosimetry with radiochromic film relative to the use arrays of ion chambers and diodes, is that it is less time-efficient. For example, commercial devices comprising arrays of ion chambers or diodes are commonly used to validate intensity modulated radiotherapy treatment (IMRT) plans delivered by linear accelerators. The time needed to set-up the array device on a linear accelerator, make the measurement, compare the measured values with the treatment plan and then pack up the device is of the order of 30 to 40 minutes. On top of this is an overhead for calibration of the array. However, this overhead is small since the array may be calibrated only once every few months during which time dozens of validation measurements would be made.

For a number of reasons it has required a significantly longer time to do a similar measurement using radiochromic film. Also, the use of film has brought other inconveniences. Firstly, the calibration of radiochromic film can be inefficient in that new production lots of film require new calibration. —The time required to set up and expose film to an IMRT plan is less than is required for the array devices. However, once the film has been exposed it must be scanned on a film digitizer and then the scan data must be processed to produce a measurement result. Usually a measurement with film will have required multiple scans and on top of that the scanning must be done at a well regulated time-after-exposure corresponding to the time-after-exposure of the calibration film. The restriction of time-after-exposure is due to the fact that the polymerization reaction initiated by the exposure continues after the exposure at a rate that diminishes with time. In practical terms this meant that several hours elapsed between exposure and scanning, meaning that the results of the measurement are only available after a considerable and inconvenient time delay. In total, the time required for the film measurement can be as much as 3× the time required to make measurements with the array devices.

As alluded to above, though the spatial resolution of a single ion chamber or diode is on the order of 1 mm, the array devices can comprise many hundreds or even a few thousand devices, but in order to cover a large area, typically 400-1000 cm2, the individual sensors can be 5-10 mm apart, severely decreasing the spatial resolution of the array device. Since these devices are used to validate treatment plans calculated at a resolution of 1 mm, or better, the array devices are not sufficient to their function.

Having spatial resolution orders of magnitude better than 1 mm, radiochromic dosimetry film could be the best choice for dose measurement and radiotherapy treatment plan validation if it were more convenient and faster to use.

SUMMARY

The present application addresses the convenience of using radiation sensitive media, and in particular, radiochromic film and provides radiation sensitive film materials and application methods to speed the process of radiation sensitive film dosimetry in a number of ways. In accordance with certain embodiments, the methods described herein may reduce the overhead required for dose calibration of radiochromic film, minimize the quantity of film required for measurement, minimize the number of scans required for film digitization, minimize the effect of scan-to-scan variability of the film digitizer, eliminate the effect of ambient temperature variation upon film digitization and/or remove the time-after-exposure constriction on film scanning due to the post-exposure changes in the radiochromic film. In total the materials and methods described herein may result in a film dosimetry process that has similar convenience and speed comparable to the ion chamber and diode array devices, but with the important and distinctive advantage of high spatial resolution.

In one aspect, the present application utilizes a previously determined calibration for a type of radiation detection medium to determine dose level in a subsequent measurement. One method for generating the calibration relationship comprises exposing locations of a radiation detection medium to a plurality of known radiation dose levels wherein each exposed location corresponds to a known radiation dose level, measuring the optical density or transmittance of each of the exposed locations, generating an array of paired data values for radiation dose level and measured density and calculating a calibration based on the array of paired density and dose values expressed as a mathematical function where dose=f(density).

In another aspect, the present application describes another method for generating a calibration curve for a type radiographic or radiochromic radiation detection medium by irradiating the radiation detection medium with at least three different radiation dose levels, each dose level being applied to an area on the detection medium to produce an exposed detection medium comprising irradiated areas, capturing an image of the exposed detection medium to form a scanned image, determining the dose level corresponding to each irradiated area and calculating the calibration for the detection medium based on the response of the scanner as a function of dose level. In accordance with particular aspects of the invention, the radiation detection medium comprises a radiochromic, self-developing film medium.

In accordance with one aspect of the present invention, areas of a radiation detection medium are exposed to known levels of radiation. The exposed radiation sensitive medium is scanned with an optical scanner. The optical scanner responds to and measures the light transmitted by the film at discrete points to create a scanned image. In accordance with this aspect of the application, the scanned image is a map of the light transmission of the radiation detection medium. The measured response is automatically associated with the corresponding radiation exposure dose and the pairs of values are plotted to provide the calibrated dose response of the radiation sensitive medium. The resulting calibration can be used to provide an indication of absorbed dose based on measurement of the exposure of the radiation sensitive medium in subsequent measurements.

DETAILED DESCRIPTION

Figure 1:
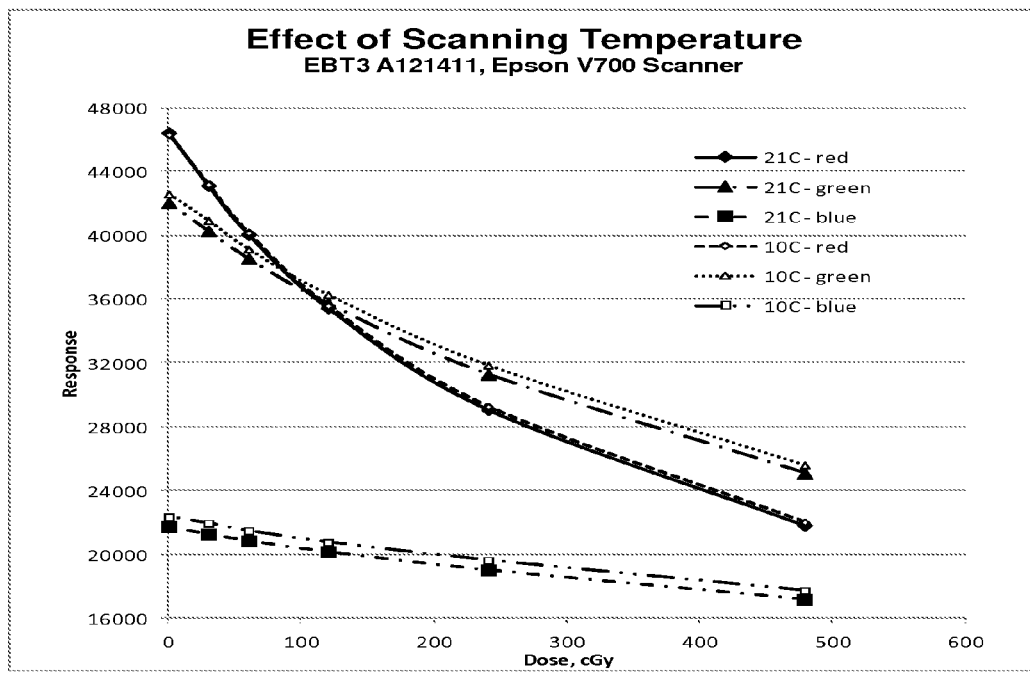
FIG. 1 is a graph of response values in each color channel plotted against dose values illustrating the effect of scanning temperature.

The following detailed description is intended to be representative only and not limiting as to the described dosimetry method. Many variations can be devised by one skilled in this area of technology, which are included within the scope of the present invention. The following detailed discussion of the various alternative and preferred embodiments will illustrate the general principles of the invention.

For the discussion below, the following terms are defined as follows:

The term "radiation detection medium" as used herein generally refers to a medium that undergoes a detectable change when exposed to radiation. The change may be immediately visible or may require a development process.

The term "radiographic film" as used herein refers to a film that forms a latent image when exposed to ionizing radiation and requires a chemical or physical development process to create a visible image.

The term "radiochromic film" as used herein generally refers to film that changes color and produces a visible image when exposed to ionizing radiation, but experiences insignificant change from exposure to visible light or other forms of non-ionizing radiation.

The term "ionizing radiation" as used herein generally refers to radiation with a level of energy that is high enough to cause atoms to lose electrons and become charged or ionized. Ionizing radiation may be in the form of high energy particles, like an alpha and beta particles, protons and neutrons, or in the form of electromagnetic waves, like gamma rays or x-rays. High energy particles and electromagnetic waves are released from the nuclei of radioactive atoms that are decaying or may be created by causing accelerated electrons to strike a metal target.

The term "spatial resolution" as used herein refers to the ability of a radiation detector to distinguish doses delivered at locations in the length domain and can be measured in terms of resolving power in units of line pairs/mm.

The term "same type" with respect to films described herein refers to films that are coated with materials containing the same active radiation-sensitive component but differ in some way in their construction. One example is that the substrate on which they are coated may differ in thickness, or the active coating may be sandwiched between two substrates, or the active coating may be of different thicknesses. Films of the same production lot are a subset of films of the same type.

An exposed location of a detection medium refers to a finite area of the detection medium that can later be measured to quantify the effects of radiation exposure. The finite area may be as small as a single measurement point, or it may encompass multiple measurement points. For example, for the purpose of scanning and measuring a radiation detection medium having an optical image, the image is usually divided into a multitude of discrete picture elements, or pixels, with a small, but finite size. Each pixel has an identifiable location with respect to the image and is associated with information that quantifies a property of the image at that location. Typically the image property that is measured is related to the optical transmittance, or optical density of the image over one or more bands of wavelengths. The size of a measurement points on the image is related to the size of a single pixel and can typically be of the order of $10^{-4}$ cm$^2$ or smaller.

An ideal film material for radiation dosimetry would have a measured response linearly proportional to dose. Calibration would be required to characterize the response of unexposed film and the change in response as a function of dose, but once this has been established measurement of an unknown dose is very straightforward. Conventional, silver-based photographic film can approach this ideal, but it is highly dependent upon the post exposure processing required to convert the latent image to a visible and measurable form. Small changes in processing conditions can alter the slope of the response curve or even cause it to become non-linear.

Radiochromic film does not require post-exposure processing, eliminating it as an error source. However, radiochromic film does not have a linear response to radiation exposure and furthermore the response changes with the time-after-exposure. In the first part this is due to the fact that the radiolysis of the film produces a colored dye. Measurement of the black image in a conventional silver film can be done with a visible light source with any bandwidth—white or colored light—because the transmission of light through the black image is independent of wavelength. Radiochromic film provides a colored dye and the transmission of a broad spectrum light source through a colored film is fundamentally non-linear. But even if transmission measurement could be done with monochromatic light the development of color from radiation exposure of the radiochromic film would be non-linear. In the second part, the radiation exposure initiates a polymerization in the active component that continues after the exposure has stopped, albeit at an ever decreasing rate. This has meant that all exposed films must be scanned at some known time-after-exposure in order that the calibration function of the calibration films is applicable to the film from which measurements are required.

The equipment of choice for measuring exposed radiochromic film is an rgb film digitizer, e.g., commercially available flatbed scanners of capable of 48 bit color depth such as Epson V700, V750, 1680 and 10000XL. The response X(D) of radiochromic film at dose D can be fit to a rational function of the type $$X(D)=A+B/(D-C)$$

where A, B and C are constants. Functions of this type are especially useful for fitting dose-response data from radiochromic film because they have a behavior consistent with the physical behavior of the film. That is, radiochromic film gets darker and darker the more it is exposed and the transmission asymptotes to a constant value. As expressed by the function the response X(D) approaches the value of A as dose D approaches infinity. Considering time-after-exposure, the responses at the various times after exposure can be fit to a family of response curves of this form where the value C changes between the different times-after-exposure. GAFCHROMIC EBT2 and EBT3 radiochromic films exhibit such a response as described in more detail below.

Furthermore, the dose responses for scan measurements of exposed EBT2 and EBT3 radiochromic films made at temperatures between approximately 50° F. and 80° F. can be fit similarly to a family of response curves where the value C changes with temperature.

A similar family of response curves can be developed for different lots of a certain type of media. For example, there is a similarity in the response functions of different lots of EBT2 and EBT3 film. Thus, if dose response is normalized to the response of an unexposed film from the same lot, that similar to the above, the dose responses of all lots can be fit to a family of response curves where the value C changes with lot.

In accordance with certain aspects, the present application provides methods and systems for improved radiation dosimetry. In accordance with one aspect, the present application illustrates how any calibration function determined for radiation sensitive films on a given scanner, and more particularly EBT2 and EBT3 radiochromic films, can be used to generate a universal calibration function. In accordance with one embodiment, the method includes:

1) Exposing films from a single lot of film to a number of known doses of radiation. The number of doses is preferably 3, or more.

2) Together with an unexposed film, scanning the exposed films on a scanner to acquire digital images. To minimize error from time-after-exposure differences these scans should be done at least 24 hours after exposure.

3) Measuring the portions of the digital images corresponding to the exposed and unexposed films. The measured values for each film in each color channel should be normalized to the values in the image corresponding to the unexposed film. The pairs of normalized dose and response values can be fit to a dose response function of the type described above. This is the universal calibration function. If desired, more than one set of response data can be used to generate the universal calibration function. In accordance with particular embodiments, determination of this calibration function can be a "one-time" event.

4) Exposing a radiotherapy treatment plan on a film of the same type and exposing a second film from the same lot to a known radiation dose. The former film is referred to as the IMRT film and latter film is referred to as the scaling film.

5) Placing the IMRT film and the scaling film together with an unexposed film from the same film lot on the scanner and scanning the films. It is assumed here that the IMRT film and scaling film have been exposed with minimal time interval.

6) Measuring the scaling film and unexposed film and together with the universal calibration curve using the data to determine a specific response function for that lot of film as determined by the zero dose and scaling dose.

7) Using the response function to convert the film response image, which includes the IMRT film and scaling films to a dose image.

The resulting dose image is then used as usual for comparison with the treatment plan.

In accordance with particularly useful aspects of the present application, the calibration overhead has been reduced to a "one-time" event (perhaps repeated on a more convenient basis such as annually, or as part of a QA plan).

In accordance with certain aspects, the exposure part of the operation has been reduced to two films—IMRT film and scaling film. The exposures, if done efficiently, should take about 10-15 minutes.

In accordance with some methods as described herein, the scan part of the protocol has been reduced to a single scan. The scanning, if done efficiently, should take about 5 minutes.

In accordance with some embodiments, comparison between the measured doses and the IMRT treatment plan can be completed in about 5 minutes.

Total time for a single IMRT can be about 20-25 minutes. This is similar to the time for the array devices.

One of ordinary skill in the art is well aware of the various methods that can be used to automatically expose areas of the radiation detection medium to different dose levels. For example, multi-leaf collimators, secondary collimators or fixed-blocks of radiation attenuating material, either alone or in combination, may be used to differentially shield the random areas during exposure to ionizing radiation. The differentially shielded portions of the radiation detection medium allow for variations in dose level without altering the ionizing radiation characteristics such as beam intensity, individual exposure duration, etc. In accordance with other aspects of the invention, variations in dose level may be obtained by altering the ionizing radiation characteristics, by changing the rate at which the exposure dose is applied or by changing the time of exposure or by any combination of any of the aforesaid means.

The linear accelerator or other source of ionizing radiation exposes areas of a radiation detection medium to known radiation dose levels, which results in a radiation dose pattern on the radiation detection medium. In accordance with one aspect of the invention, the optical transmission of each of the exposed areas is measured and associated with the corresponding known radiation dose levels. In accordance with certain embodiments of the present invention, the radiation detection medium is scanned using an optical film scanner to produce a scanned image of the film. In accordance with particularly useful embodiments of the invention, the scanned image is analyzed through the use of a software program that takes measurements over the scanned image. Based on certain criteria, the software takes representative measurements for the exposed areas of the radiation detection medium. The measured value for each exposed area is then matched to an associated radiation exposure dose and the pairs of values are used to generate a calibration curve for the radiation detection medium.

The exposed areas of the radiation detection medium may be measured through the use of a scanner, such as those typically used for this purpose. Representative examples of film scanners that may be used include, without limitation, Vidar VXR-16, Epson Expression 1680, Microtek 9800XL, etc. The equipment of choice for measuring exposed radiochromic film is an rgb film digitizer, e.g., Epson V700, V750, 1680 and 10000XL. Typically, the scanner converts the exposed radiation detection medium to an array of pixels having values representing the optical transmission at each point or location on the medium. Particularly useful scanners provide a digital image in a multiplicity of response channels and the conversion of the measurement film image from scanner response to radiation dose values is performed using the association between the dose values and the multiplicity of the scanner response values of the calibration films Radiation dosimetry methods utilizing scanners with a multiplicity of response channels are described in more detail in U.S. patent application Ser. No. 12/710,004, published as Pub. No. US 2010/0213362, the contents of which are hereby incorporated by reference.

Individual radiation dose levels depend on a number of factors, such as the radiation source, time of exposure, rate of exposure, distance between the source of the radiation and the radiation detection medium, etc. Commercially available linear accelerators can typically deliver about 600 cGy per minute. Since most fractionated radiotherapy requires dose levels less than about 1,000 cGy, individual radiation exposures are typically on the order of a few seconds to a few minutes. Calibration of the radiation detection medium in accordance with the present invention typically involved radiation dose levels in the range of those expected to be used in the radiotherapy treatment. For example, typical radiation dose levels for IMRT treatment may fall within the range of from about 1 cGy to about 500 cGy, more particularly from about 1 cGy to about 200 cGy and in accordance with particular aspects of the invention, from about 1 cGy to about 100 cGy.

The radiation detection medium can be any material or device capable of responding in a repeatable and consistent way to radiation exposure. One embodiment of the present invention provides a radiation dosimetry method wherein the radiation detection medium is a radiographic or radiochromic film. In accordance with particular embodiments, a radiochromic film is used. GAFCHROMIC® radiochromic films manufactured by Ashland Specialty Ingredients are particularly useful. Specific examples of radiochromic films suitable for use in the present invention include, but are not limited to, EBT2, EBT3 and those disclosed in U.S. patent application Ser. No. 10/229,489, published as Pub. No. 2003/0129759 to Lewis et al., on Jul. 10, 2003, which is incorporated herein in its entirety.

Although the present application is not limited to a particular type of radiation detection medium, the following description relates to an embodiment of the application based on the use of a particularly useful type of film. GAFCHROMIC® radiochromic film is self developing, not significantly sensitive to normal room light, and can be cut to a desired size. Exposure to ionizing radiation causes the radiochromic film to immediately change color, typically becoming darker. The degree of darkening is proportional to exposure and can be quantitatively measured with a densitometer or optical film scanner.

The active component in the GAFCHROMIC® film media is a micro-particulate, radiation sensitive monomer that is dispersed in a polymer matrix and coated onto a polyester film base. When the active monomeric component is exposed to ionizing radiation, a polymerization reaction is initiated, resulting in the production of a dye polymer. Since this polymer is by nature, a dye, the exposure produces coloration within the film. The active ingredient in accordance with particular embodiments comprises a long chain fatty acid belonging to a class of molecules known as diacetylenes. Many members of the diacetylene family are characteristically radiation sensitive only when there is intermolecular order, as, for instance, in a crystalline or micellar state. Suitable acetylenic compounds have the structure $A\text{-}(CH_2)n\text{-}C{=}C\text{---}C{=}C\text{---}(CH_2)m\text{-}B$, where n and m are both independently an integer of from about 0 to 20, more particularly from about 6 to 14, and A and B are independently a methyl group, a carboxyl group or metal carboxylate group. When exposed to radiation, active diacetylenes undergo a solid-state polymerization reaction producing a dye polymer referred to as a polydiacetylene. The color and spectral absorbance of polydiacetylene is specific to the particular molecular structure, but preferably the color change is clearly visible on the radiation sensitive film. The color change is frequently cyan blue, purple or magenta.

Specific examples of such polyacetylenes include, but are not limited to, pentacosa-10,12-diynoic acid; 13,15-octacosadiyne and docosa-10,12-diyne-1,22-dioic acid. Of these, pentacosa-10,12-diynoic acid is particularly useful since it provides unusually high sensitivity to ionizing radiation exposure. It is to be understood however, that dispersions of other normally crystalline, color developing polyacetylenes having a conjugated structure can be employed alone or in admixture with the preferred diynes as the image receptive layers of the present invention. Such compounds include the diynes of the above structure wherein the A and/or B moieties, in addition to lower alkyl or carboxyl, can also be hydroxy, amido, lower alkyl substituted amido, an aliphatic or aromatic carboxylate ester group having up to 10 carbon atoms, a mono- or di-valent carboxylate metal salt group, halo, carbamyl, lower alkyl substituted carbamyl or tosyl, as well as the corresponding triyne and tetrayne products of the above polyacetylenes having from about 20 to 60 carbon atoms and a conjugated structure. Examples of these compounds include 10,12-docosadiynediol, the ditoluene-p-sulfonate of 9,11-eicosadiynoic acid, the monoethyl ester of 10,12-docosadiynedioic acid, the lithium, sodium or potassium salt of 10,12-pentacosadiynoic acid, the zinc salt of heneicosa-10,12-diynoic acid, the manganese salt of eicosa-5,7-diynoic acid, 10,12-docosadiyne chloride, 10,12-pentacosadiyne (m-tolyl-urethane), 10,12-pentacosadiyne {[*butoxyl-carbonyl)-methyl]urethane}, N-(dimethyl)-10,12-pentacosadiynamide, N,N'-bis(a 1-methylbenzy-1) 10,12-pentacosadiyndiamide and the like. In addition, the diacetylenes for use in accordance with the invention generally may also have the formula:

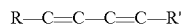

wherein R and R' are, for example, both $CH_2$—O—CON—H—$(CH_2)_5CH_3$. Such diacetylenes polymerize in the solid state either upon thermal annealing or exposure to high energy radiation. Suitable compounds are described in U.S. Pat. Nos. 5,420,000, 4,970,137, and 4,734,355, the contents of each of which are incorporated herein by reference. Preferably, the polyacetylenic compound has at least two conjugated acetylenic linkages and contains from about 10 to 60 carbon atoms.

Suitable compounds, which selectively absorb incident low energy photon radiation, are the metal halides and combinations thereof of Group I of the Periodic Table. Particularly useful are Group I metal chlorides, bromides and iodides. These compounds may be added in an amount effective to selectively absorb the incident low energy photon radiation, and generally in an amount of from about 0.1% to 50.0%, and more particularly from about 2.5% to 20% by weight of the dispersion of the coating as described hereinafter.

In accordance with some aspects of the invention, such halides are selected from the group consisting of cesium and rubidium halides and in particular, cesium chloride, cesium bromide, cesium iodide and combinations thereof.

In addition, it is possible to add an additional compound, which may be a metal ion chelating agent or sequestering agent. The chelating agent can be added in amounts of from about 0.01% to 10.0%, and more particularly from about 0.1% to 2% by weight, based on the weight of the diacetylene compound. Typical chelating agents include disodium ethylenediaminetetraacetate, sodium oxalate, citric acid, sodium citrate, sodium tartrate, sodium polyphosphate, potassium hypophosphate, sodium diethyldithiocarbamate, the sodium salt of N,N,N',N'-ethylenediaminetetra(methylenephosphonic acid), the sodium salt of 1-hydroxyethane-1,1-diphosphonic acid and combinations thereof.

An antioxidizing agent may also be added to the composition, usually in an amount of from about 0.01% to 5%, and more particularly from about 0.1 to 1% by weight of the weight of the diacetylene component. Suitable antioxidizing agents include propyl gallate, Tenoxo 6 (Tenox® is a trademark of the Eastman Chemical Company), Tenox® 2, Tenox® 7, Tenox® 20, sodium diethyldithiocarbamate, citric acid, sodium citrate, ascorbic acid, alkali metal sulfides and sulfites, 3-tert-butyl-4-hydroxy-5-methyl-phenyl sulfide, butylated hydroxytoluene, butylated hydroxyanisole, tert-butylhydroquinone, hydroxylamine and hydroxylamine hydrochloride.

The active layer of the film containing the acetylenic component may also be sandwiched between two substrates in which one or both of the substrates may have the capability to filter or absorb light in the UV and/or visible wavelength regions. At least one of the substrates should be transparent in at least part of the visible spectrum.

Particularly useful as substrates are thin, flexible films made from materials such as polyethylene teraphthalate, polyethylene, polypropylene, cellulose acetate and the like.

In accordance with a particular method for preparing a radiochromic film useful herein, the polyacetylenic compound is dispersed in a non-solvating liquid and may be ripened or aged to maximize its radiation sensitivity. This dispersion may also contain a dissolved polymeric binder. Examples of binders include, but are not limited to, gelatin, polyvinyl acetate, polyvinyl alcohol and poly vinyl pyrrolidone, agar, xanthan gum and polymers and copolymers containing maleic acid or acrylic acid residues, or salts thereof. The liquid dispersion is then applied onto the surface of a film, e.g., a polyester or similar film, and the coating is then dried. In particular, the normally crystalline or molecularly ordered polyacetylenic compound is dispersed into the non-solvating liquid in a concentration of from about 2 to 50% based on the combined weights of the polyacetylenic compound, the non-solvating liquid and the polymeric binder dissolved therein.

The thus mixed composition is then applied as a layer onto a substrate or support layer. Examples of substrates or supports that may be used include, but are not limited to, polymeric, metallic, glass, silicon and gallium arsenide. In accordance with a particular embodiment of the invention, the substrate or support layer may be a polymeric film which is permeable to low energy x-rays. The thus coated substrate is then dried at a temperature from about ambient up to about 100° C. but below the distortion temperature of the substrate and below the decomposition temperature of any of the components of the coating or the melting point of the polyacetylene compound therein. The drying operation is generally conducted over a period of from about 20 seconds to about 10 hours and is typically effected at 15° to 60° C. for a period of from about 1 minute to about 5 hours.

The film thus formed is sensitive to radiation and, upon irradiation, a polymerization process is initiated in the polyacetylenic compound resulting in an immediate change in the color of the coating. The color darkens in proportion to the radiation exposure. The degree of darkening may be measured with a number of instruments including densitometers, spectrophotometers and film scanners. Generally when making such measurements, the color change of a transparent film sample would be assessed by measuring the proportion of light transmitted through the sample. Similarly, film coated on an opaque film base would be appropriately examined by measuring the proportion of light reflected from the sample.

Since the film darkens in proportion to radiation exposure, it is possible to measure the darkening and use this measurement as a means for determining the amount of the radiation exposure based on the calibration determined as described herein. Thus, the film may be employed as a radiation dosimeter, to measure and map radiation fields. Alternatively, the film may be used to record visual images such as those produced by radiographs, or autoradiographs.

The radiation may be any type of ionizing radiation such as alpha particles, beta particles, x-rays, Gamma rays, short wavelength UV, neutrons or charged particle radiation. These particles or rays may be formed by decaying radioactive atoms, or by accelerated electrons or other charged particles striking a metal target or causing a discharge in a volume of gas. In one embodiment of the present invention the radiation is gamma radiation produced by iridium, preferably iridium-192. In another embodiment of the present invention the radiation is x-ray radiation. X-rays are produced when electrons collide with the atoms and nuclei of a metal target.

It would be possible to use any radiographic and radiochromic films used to measure or record exposure to radiation in developing a calibration as described herein. However, conventional radiographic films present at least four substantial difficulties that are not applicable to the use of radiochromic film. Firstly, radiographic films are light sensitive. This would complicate the calibration procedure. Secondly, radiographic films may be extremely sensitive to small levels of contaminants that could desensitize the active layer or cause objectionable levels of fog. Thirdly, radiographic films are chemically processed to develop the image. The chemical solutions are caustic and may react adversely with the printing inks. Fourthly, the radiographic films have an energy-dependent response radiation. Since the energy spectra of radiation sources employed in radiotherapy may vary substantially with the depth of penetration in the patient and the size of the patient this can lead to uncertainties in dose measurements made with radiographic films.

The following, non-limiting examples illustrates particular aspects of the present invention.

Example 1

This Example pertains to the scan-to-scan variability of an optical scanner. A piece of Gafchromic EBT3 radiochromic film was placed on the glass scan window of an Epson 10000XL scanner. From time to time over the period of a day the film was scanned in transmission mode to acquire a 48-bit rgb digital images of the radiochromic film with a spatial resolution of 72 dpi. Areas corresponding to the radiochromic film in the digital images were measured using a software application, FilmQA Pro. The measured values are shown in Table 1, below. Inspection of these values shows that they have variability of about 0.5% about the mean value.

TABLE 1

| Image # | Response value, red channel |
|---|---|
| 1 | 48012 |
| 2 | 47994 |
| 3 | 48304 |
| 4 | 48106 |
| 5 | 47858 |
| 6 | 48114 |
| Mean | 48065 |
| Maximum | 0.50% |
| Minimum | −0.43% |

Similar results were obtained from like measurements made in the green and blue color channels. It is believed that the differences between the scan images occur for a number of reasons including temperature variations during the day, instability of the scanner's light source and variability within the various opto-electronic measurement circuits of the scanner. When the radiochromic film and scanner are used to make measurements of radiation dose exposed on the film, the overall variability leads to error in those dose measurements.

Example 2

This Example demonstrates error in dose measurement due to the type of variability evidenced in Example 1. Three pieces of Gafchromic EBT3 radiochromic film Lot A101711 were exposed to calibrated X-ray radiation doses of 501.1 cGy, 253.2 cGy and 123.7 cGy. Together with a piece of unexposed film from the same lot, and about two weeks after they had been exposed, the films were placed on an Epson V700 scanner and from time-to-time over a period of about 16 hours throughout the day 48-bit rgb digital images were acquired with a spatial resolution of 72 dpi. The purpose of waiting for two weeks after exposure of the films is to allow the films to equilibrate. It is well known that the Gafchromic EBT3 radiochromic film continues to darken after exposure, but the rate of change diminishes rapidly with time. After two weeks the rate of change is too small to be measured over a 16 hour period as was used in the data acquisition.

Areas corresponding to the radiochromic film samples in the digital images were measured using the FilmQA Pro software. The values in the red color channel measured in the first image in the sequence were plotted against the dose values and the data was fitted with a mathematical function of the type $$D = A + B/(C-R)$$

where D is the exposed dose, R is the measured response in the digital image and A, B and C are constants. This function was then applied to convert the response values in the first digital image to dose values. The measured values in the dose image are given in Table 2 and are compared with the calibrated exposure values.

TABLE 2

| Calibrated Dose, cGy | Calculated Dose, cGy dose |
|---|---|
| 501.1 | 501.4 |
| 253.2 | 253.6 |
| 123.7 | 124.0 |
| 0.0 | 0.0 |

There is a close correspondence of the calculated and calibrated doses, the differences being due to small errors in applying the calibrated dose, in scanning and measuring the film images and in the uniformity of the radiochromic film.

The values A, B and C determined for the fitting function from the first image in the sequence (Image #1) were applied to convert each of the subsequent scan images to dose images. FilmQA Pro software was used to measure the dose values of the radiochromic films. The values are given in Table 3.

TABLE 3

| Image #1 Calculated Dose, cGy | Image #2 Calculated Dose, cGy | Image #3 Calculated Dose, cGy | Image #4 Calculated Dose, cGy | Image #5 Calculated Dose, cGy | Image #6 Calculated Dose, cGy |
|---|---|---|---|---|---|
| 501.4 | 508.4 | 502.3 | 501.8 | 501.0 | 495.9 |
| 253.6 | 257.8 | 254.6 | 254.0 | 253.7 | 250.1 |
| 124.0 | 126.9 | 124.5 | 124.2 | 124.1 | 121.4 |
| 0.0 | 1.9 | 0.4 | 0.2 | 0.1 | −1.4 |

It is evident that there is considerable scan-to-scan variability of the doses calculated from the measurements and the variability will be the source of measurement error. The % differences in the calculated doses relative to the doses from the first digital image are shown in Table 4. Dose variations up to 2.4% in dose are seen.

TABLE 4

| Image #1 Dose, cGy | Image #2 Difference relative to Image #1 | Image #3 Difference relative to Image #1 | Image #4 Difference relative to Image #1 | Image #5 Difference relative to Image #1 | Image #6 Difference relative to Image #1 |
|---|---|---|---|---|---|
| 501.4 | 1.4% | 0.2% | 0.1% | 0.1% | 1.1% |
| 253.6 | 1.7% | 0.4% | 0.1% | 0.0% | 1.4% |
| 124.0 | 2.4% | 0.4% | 0.2% | 0.1% | 2.1% |
| 0.0 | — | — | — | — | — |

Example 3

This Example shows that scaling the response values in the Images of Example 2 so as to equalize the measured values of the unexposed film leads to a marked reduction in the dose variability of the exposed film.

Table 5 lists the red channel values measured for each of the films in the Images described in Example 3. As noted before there is considerable variability in the values of the unexposed film.

TABLE 5

| Calibrated | Red channel response values | | | | | |
|---|---|---|---|---|---|---|
| Dose, cGy | Image 1 | Image 2 | Image 3 | Image 4 | Image 5 | Image 6 |
| 501.1 | 22661 | 22527 | 22644 | 22654 | 22669 | 22768 |
| 253.2 | 29527 | 29360 | 29486 | 29512 | 29522 | 29668 |
| 123.7 | 36240 | 36044 | 36207 | 36227 | 36235 | 36417 |
| 0.0 | 47918 | 47674 | 47866 | 47894 | 47910 | 48098 |

The response values of the films in Image X are modified by applying a scale factor equal to the response value of unexposed film in Image 1 divided by the response value of unexposed film in Image X. By this means the response values of the unexposed film in the images are equalized. At the same time the relative values of the exposed films to the unexposed film are maintained. The scaled values are shown in Table 6.

TABLE 6

| Calibrated | Red channel response values - after scaling to equalize responses of unexposed film | | | | | |
|---|---|---|---|---|---|---|
| Dose, cGy | Image 1 | Image 2 | Image 3 | Image 4 | Image 5 | Image 6 |
| 501.1 | 22661 | 22642 | 22669 | 22665 | 22672 | 22682 |
| 253.2 | 29527 | 29510 | 29517 | 29527 | 29527 | 29556 |
| 123.7 | 36240 | 36228 | 36247 | 36245 | 36240 | 36280 |
| 0.0 | 47918 | 47918 | 47918 | 47918 | 47918 | 47918 |

As described in Example 2 the dose values, D, and response values, R, for Image 1 were fitted to a function $$D=A+B/(C-R)$$

describing the radiation dose as a function of response value and defining the values of the coefficients A, B and C. These same coefficients were applied to calculate dose values for Images 2 to 6 and the values are shown in Table 7.

TABLE 7

| Calculated Doses, cGy - after scaling to equalize responses of unexposed film | | | | | |
|---|---|---|---|---|---|
| Image #1 | Image #2 | Image #3 | Image #4 | Image #5 | Image #6 |
| 501.4 | 501.4 | 502.4 | 501.0 | 500.8 | 500.3 |
| 253.6 | 253.6 | 254.0 | 253.8 | 253.6 | 252.9 |
| 124.0 | 124.0 | 124.2 | 123.9 | 124.0 | 123.4 |
| 0.0 | 0.0 | 0.0 | 0.0 | 0.0 | 0.0 |

After scaling the images to equalize the response values of the unexposed films there is notably better consistency of the dose values of the exposed films as shown in the following Table. Comparing the values in Table 8 to the values in Table 4 it is apparent that the response value scaling operation has reduced the variability from 2.5% to 0.5%.

TABLE 8

| Dose, cGy | Difference relative to Image #1 | Difference relative to Image #1 | Difference relative to Image #1 | Difference relative to Image #1 | Difference relative to Image #1 |
|---|---|---|---|---|---|
| 501.1 | 0.0% | 0.2% | 0.1% | 0.1% | 0.2% |
| 253.2 | 0.0% | 0.2% | 0.1% | 0.0% | 0.3% |
| 123.7 | 0.0% | 0.1% | 0.1% | 0.0% | 0.5% |
| 0 | — | — | — | — | — |

Example 4

This Example is included to demonstrate the effects of temperature on the measured response of radiochromic film and to show how those effects can be attenuated by scaling the response values to equalize certain measured responses.

Five samples of a radiochromic film, Gafchromic EBT3 lot# A121411, were exposed to different doses of x-rays ranging from about 30 cGy to about 480 cGy. Together with a piece of unexposed film from the same lot, and about four days after the films had been exposed, the films were placed on an Epson V700 scanner and scanned in transmission to acquire a 48-bit rgb digital image with a spatial resolution of 72 dpi. The temperature on the scanner was measured at 21° C. The scanner was placed in a cold room and about 3 hours later the films were placed on the scanner and another digital image was acquired. This time the temperature on the scanner was 10° C. The rate of post-exposure change four days after exposure is known to be very slow. After four days any changes in response due to post-exposure growth would be undetectable over the 3-hour period of the experiment.

The response values of the portions of the two digital images corresponding to the films were measured using the FilmQA Pro software. The response values for each color channel in each image were plotted against the dose values. The results are shown in FIG. 1. While the response values in the red color channel at the two temperatures differ by only a small amount the response values in the green and blue color channels are very different.

Figure 2:
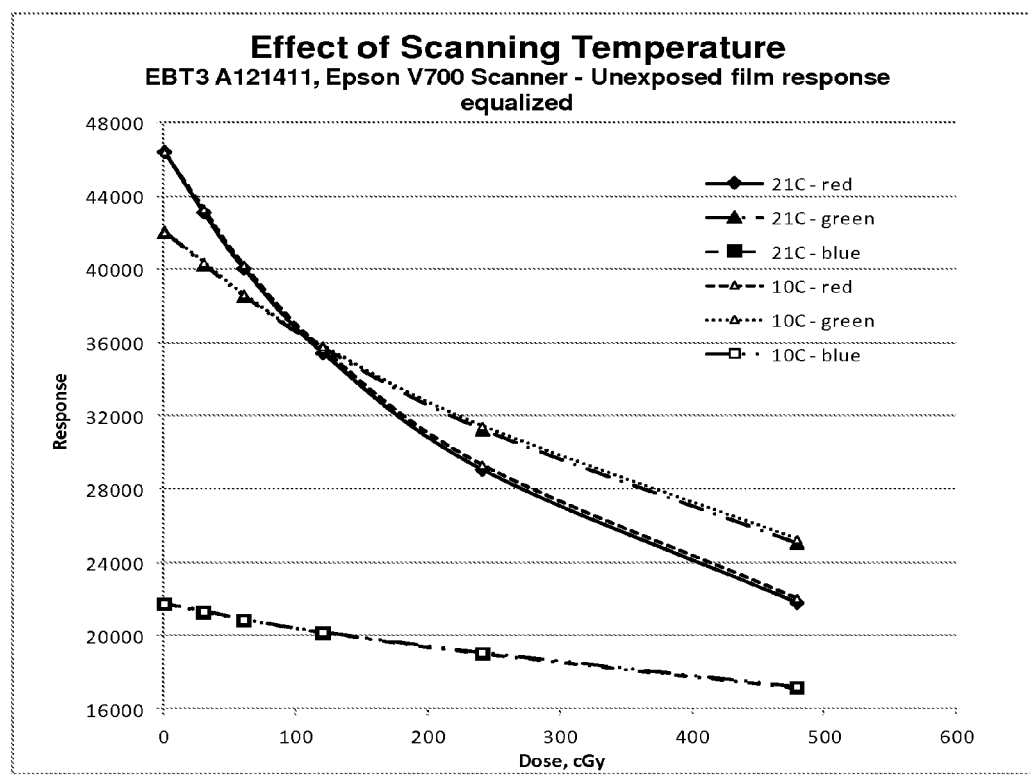
FIG. 2 is a graph of response values in each color channel plotted against dose values after equalizing the responses of the unexposed films in the 10° C. and 21° C. images.

A compensation that could be made is to scale the response values measured in the image scanned at 10° C. so that the response values for unexposed film in the 10° C. and 21° C. images are equalized. The effect of this equalization can be seen from the data presented in FIG. 2. It shows that after equalizing the responses of the unexposed films in the 10° C. and 21° C. images the measured responses of the exposed films also become similar. However, close inspection shows that the response curves at the different temperatures are slightly divergent.

Example 5

The experiment of Example 4 was repeated with EBT3 film of a different lot number—A110211. Results similar to those presented in Example 4 were obtained. The dose-response characteristics measured in the 21° C. image were used to define the coefficients of a dose-response function and this function was then used to calculate the exposure doses represented in the digital image obtained at 10° C. The data in Table 9 shows the result of these calculations and shows that the calculated doses are considerably different than the calibrated doses used for the exposures. The discrepancies in the doses for the green and blue color channels are particularly large. It is evident that if dose measurements are to be made with film scanned at one temperature the film should be scanned at the same temperature at which the dose-response calibration was determined unless some other means for compensation is applied.

TABLE 9

| Dose exposure on film, cGy | Dose measured on film - single channel protocol | | |
|---|---|---|---|
| | Red channel | Green channel | Blue channel |
| 0.0 | <0 | <0 | <0 |
| 31.9 | 30.5 | 19.2 | <0 |
| 59.5 | 58.0 | 46.8 | 9.3 |
| 121.6 | 119.0 | 108.6 | 70.3 |
| 242.8 | 236.7 | 223.6 | 175.3 |
| 487.9 | 477.7 | 458.2 | 397.1 |

As a first step in applying compensation for temperature differences the responses can be scaled to equalize the measured values for unexposed film scanned at 10° C. to the values measured at 21° C. When this is done the dose measurements from the image scanned at 10° C. more closely correspond to the calibrated exposure values in all channels, but the measured values still diverge from the calibrated values as the dose level increases.

TABLE 10

| Dose exposure on film, cGy | Dose measured on film - triple-channel protocol | | |
|---|---|---|---|
| | Red channel | Green channel | Blue channel |
| 0.0 | 0.6 | 1.0 | 0.6 |
| 31.9 | 30.1 | 30.1 | 30.1 |
| 59.5 | 57.6 | 58.1 | 57.8 |
| 121.6 | 118.2 | 119.7 | 118.9 |
| 242.8 | 236.3 | 238.0 | 237.0 |
| 487.9 | 478.7 | 478.2 | 478.4 |

A second compensation was then applied in which the measured responses between zero and 487.9 cGy were scaled in proportion to the calibrated exposure dose value divided by the measured value. Performing this operation yields the results presented in Table 11. The scaled values obtained from the 10° C. image now correspond closely with the calibrated exposure values. This result demonstrates that a two-point resealing of measured film responses can be used to compensate for the effects of temperature difference between scans.

TABLE 11

| Dose exposure on film, cGy | Dose measured on film - triple-channel protocol | | |
|---|---|---|---|
| | Red channel | Green channel | Blue channel |
| 0.0 | 0.5 | 0.9 | 0.6 |
| 31.9 | 30.7 | 30.6 | 30.7 |
| 59.5 | 58.7 | 59.8 | 59.0 |
| 121.6 | 120.7 | 122.3 | 121.4 |
| 242.8 | 241.2 | 243.0 | 242.0 |
| 487.9 | 487.9 | 487.9 | 487.9 |

Example 6

This Example is included to show the effect of post-exposure changes in the measured response of radiochromic film. Samples of Gafchromic EBT3 radiochromic film, lot number A101711, were exposed to several calibrated radiation doses between about 30 cGy and 480 cGy over a period of about 5 minutes. After the exposure, the films were placed on an Epson 10000XL scanner together with a piece of unexposed film from the same lot. From time-to-time over a period of several days the films were scanned in transmission mode to acquire 48-bit rgb digital images of the radiochromic films with a spatial resolution of 72 dpi. Portions of the digital images corresponding to the film samples were measured using FilmQA Pro software. The results for the red color channel are presented in Table 12

TABLE 12

| Calibrated exposure dose, cGy | Response values, red channel after exposure | | | | | |
|---|---|---|---|---|---|---|
| | 65 min | 120 min | 255 min | 490 min | 1440 min | 4800 min |
| 482.6 | 22346 | 22208 | 22131 | 21967 | 21653 | 21585 |
| 238 | 29595 | 29456 | 29412 | 29218 | 28882 | 28869 |
| 118.1 | 36155 | 36037 | 36046 | 35848 | 35530 | 35584 |
| 60.2 | 40869 | 40777 | 40820 | 40648 | 40351 | 40490 |
| 31.5 | 44055 | 43992 | 44113 | 43959 | 43691 | 43881 |
| 0 | 48012 | 47994 | 48215 | 48106 | 47858 | 48114 |

The data show the effect of post-exposure change in film response. The changes in response values are relatively large at short times after exposure and become smaller as the post-exposure time increases. However there is significant variability in the measured values of the unexposed film and this effect masks the effect of post-exposure changes. The variability can be removed by scaling the response values within each digital image so as to equalize the responses of the unexposed films. Scaling the responses so equalize the unexposed film values to the value at 65 minutes after exposure yields the results shown in Table 13.

TABLE 13

| Calibrated exposure dose, cGy | Response values, red channel after exposure | | | | | |
|---|---|---|---|---|---|---|
| | 65 min | 120 min | 255 min | 490 min | 1440 min | 4800 min |
| 482.6 | 22346 | 22217 | 22038 | 21925 | 21723 | 21540 |
| 238 | 29595 | 29467 | 29289 | 29161 | 28975 | 28808 |
| 118.1 | 36155 | 36051 | 35894 | 35778 | 35644 | 35509 |
| 60.2 | 40869 | 40793 | 40648 | 40568 | 40481 | 40405 |
| 31.5 | 44055 | 44009 | 43927 | 43874 | 43832 | 43789 |
| 0 | 48012 | 48012 | 48012 | 48012 | 48012 | 48012 |

Figure 3:
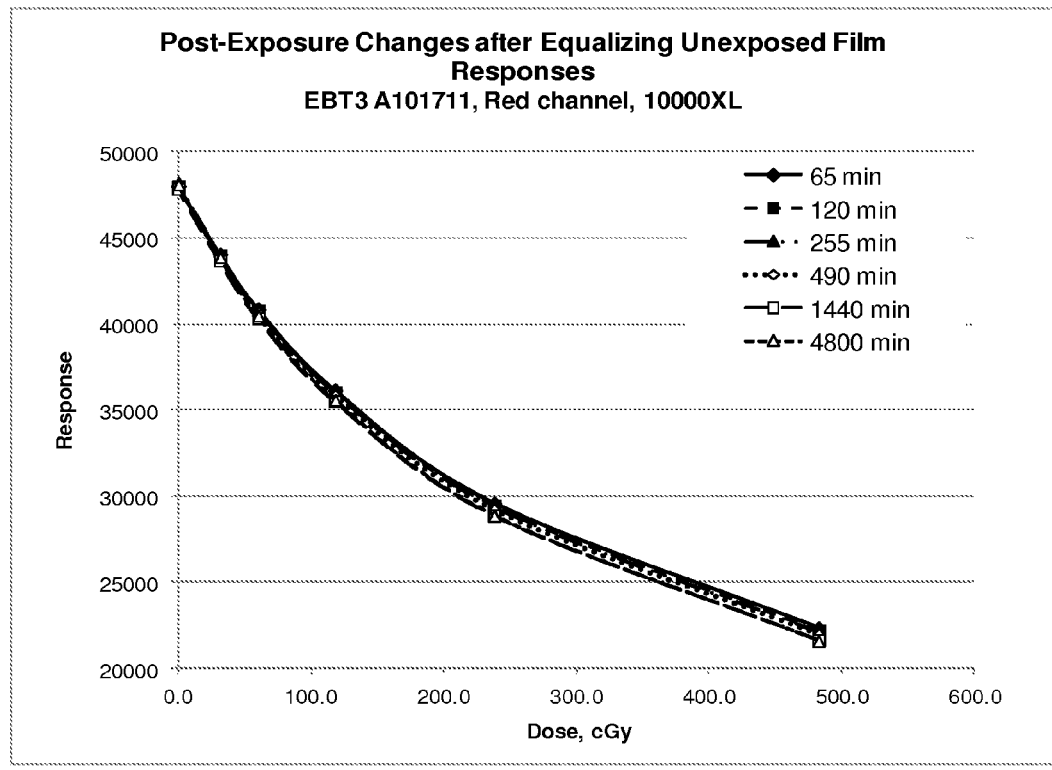
FIG. 3 is a graph of response values plotted against dose values for post-exposure changes after equalizing unexposed film responses as described in Example 6.

The data from Table 13 is plotted to visualize the differences. This is presented in FIG. 3 and shows that the response values of the exposed films diverge in proportion to the calibrated exposure dose and to the time-after-exposure. As in Example 5 a second scaling is applied to the images to equalize the measures response values at the highest dose, 482.6 cGy.

Figure 4:
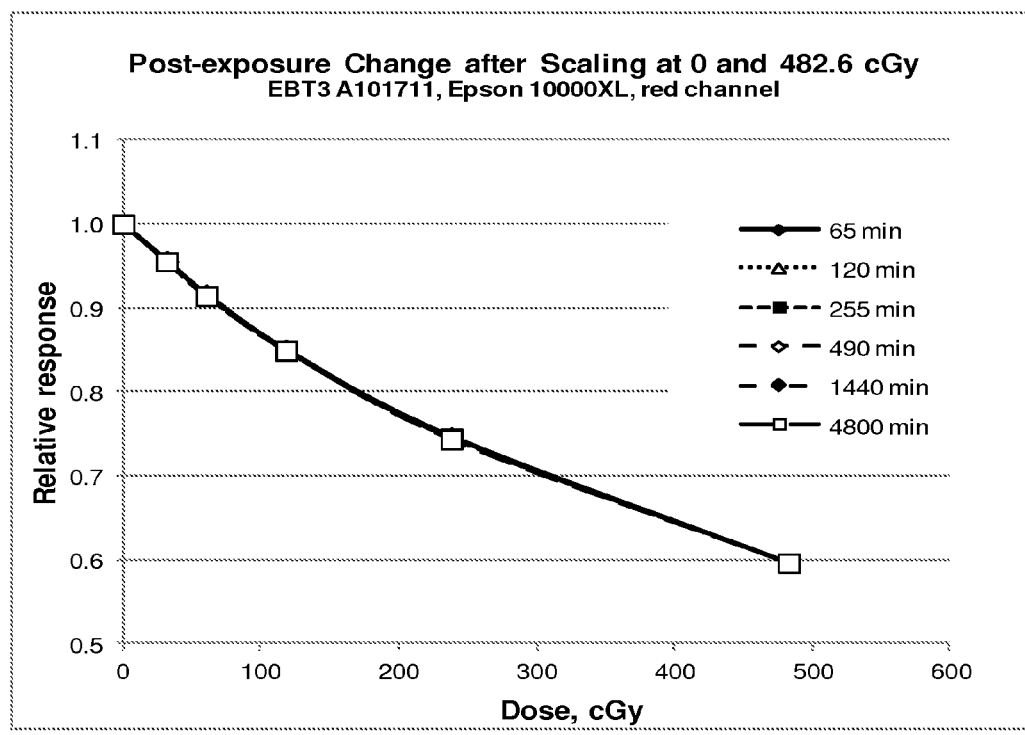
FIG. 4 is a graph of response values plotted against dose values after applying the second scaling in Example 6.

FIG. 4 shows the data after the second scaling has been applied. From inspection it can be seen that the scaled response values are independent of the time-after-exposure.

The responses in the green and blue channels behave in a similar fashion, i.e., when scaled at two points the response values are independent of time-after-exposure.

Example 7

From the six digital images obtained for Example 6, the image obtained at 490 minutes after exposure was selected. The dose-response data was plotted and fit to a function of the type described in Examples 2 and 3 defining the values of the coefficients A, B and C.

The function was then applied to the response data from each of the images to convert the images from scanner response space into dose space. Finally the dose values corresponding to the films in the images were measured. The values are recorded in Table 14. Inspection of these values shows that apart from the values measured in the image of the calibration film acquired 490 minutes after exposure the values have a poor correspondence to the calibrated dose values delivered to the films. In general the doses measured from images acquired prior to 490 minutes are smaller than the dose values from the calibration image while the doses measured from images acquired later than 490 minutes after exposure show doses greater than those from the calibration image. This pattern is consistent with the post-exposure growth characteristic if the radiochromic film.

TABLE 14

| Dose delivered to calibration film, cGy | Dose (cGy) measured from image 490 min after exposure | Doses measured from images acquired at various times after exposure | | | | |
|---|---|---|---|---|---|---|
| | | 65 min | 120 min | 255 min | 1440 min | 4800 min |
| 0 | 0.2 | 0.2 | 0.2 | 0.0 | 0.7 | 0.3 |
| 31.5 | 31.1 | 29.4 | 30.0 | 29.0 | 32.2 | 32.0 |
| 60.2 | 61.5 | 58.3 | 59.5 | 58.8 | 63.0 | 63.5 |
| 118.1 | 118.0 | 112.4 | 114.7 | 113.9 | 120.0 | 122.2 |
| 238.0 | 235.9 | 224.8 | 229.7 | 228.8 | 239.9 | 245.8 |
| 482.6 | 486.3 | 463.3 | 475.0 | 472.7 | 495.0 | 505.5 |

A two-point scaling process was applied to the scanned images. First the images were scaled to equalize the response values for the unexposed film to the response value measured in the 490 minute calibration image. Then a dose map was derived from each image based on the fitted dose-response function derived from the calibration image. Finally the dose map for each image was scaled to equalize the dose values of the film given the 486 cGy calibration exposure. The results are displayed in Table 15. After the scaling all the dose values measured from the images acquired before and after the calibration image are closely consistent with the corresponding values in the calibration image. Similar results are obtained from measurements in the green and blue color channels.

TABLE 15

| Dose delivered to calibration film, cGy | Dose (cGy) measured from calibration film image | Doses measured from images acquired at various times after exposure after scaling | | | | |
|---|---|---|---|---|---|---|
| | | 65 min | 120 min | 255 min | 1440 min | 4800 min |
| 0 | 0.0 | 0.0 | 0.0 | 0.0 | 0.0 | 0.0 |
| 30.5 | 30.8 | 30.6 | 30.5 | 30.7 | 30.8 | 30.5 |
| 60.6 | 61.1 | 60.7 | 60.4 | 60.8 | 61.0 | 60.6 |
| 116.6 | 117.1 | 117.2 | 116.6 | 116.7 | 117.0 | 116.6 |
| 234.6 | 234.1 | 234.2 | 233.5 | 233.6 | 235.0 | 234.6 |
| 482.6 | 482.6 | 486.6 | 486.6 | 486.6 | 486.6 | 482.6 |

The results demonstrate that the effects of post-exposure growth can be compensated for by a using simple scaling process. Thus a number of films from a given production lot would be exposed to known doses. Together with an unexposed film from the same lot, all films would be scanned together at the same time-after-exposure. In practice it would not be necessary that the time-after-exposure be identical for all films, but rather the differences in timing would be small relative to the elapsed time-after-exposure. A function would be applied to fit the dose-response data from the calibration films. Together with the fitted coefficients, this becomes the master calibration function. Given a film from the same production lot from which dose measurements are to be made, two additional films from the same production lot would be required; a piece of unexposed film and a piece of film exposed to a known dose immediately before or after the film to be measured. The three films would then be scanned together at a long time-after-exposure compared to the timing differences between the two exposed films. The digital image would be scaled to equalize the response values corresponding to the unexposed film to the response values of the unexposed calibration film and then converted to a dose image using the master calibration function. Finally the dose image would be scaled so the dose values correspond to the film exposed to a known dose.

Example 8

This example is included to show that dose-response information obtained from two scanners of the same type can be scaled to establish a correspondence in a way similar to that described in the previous Examples.

The film samples described in Examples 6 and 7 were used and were scanned on four different Epson 10000XL scanners at different times-after-exposure to acquire 48-bit rgb digital images at a spatial resolution of 72 dpi. The images from all scanners were scaled to equalize the response values of the unexposed films to the value of the unexposed film from Scanner 1. Measurements were then made in those areas of the images corresponding to the film exposed to the greatest dose (482.6 cGy). The response values in the image from Scanner X were then scaled based on the response difference between unexposed film and 482.6 cGy exposed film in the image from Scanner 1 divided by the similar response differences in the image from Scanner X.

Figure 5:
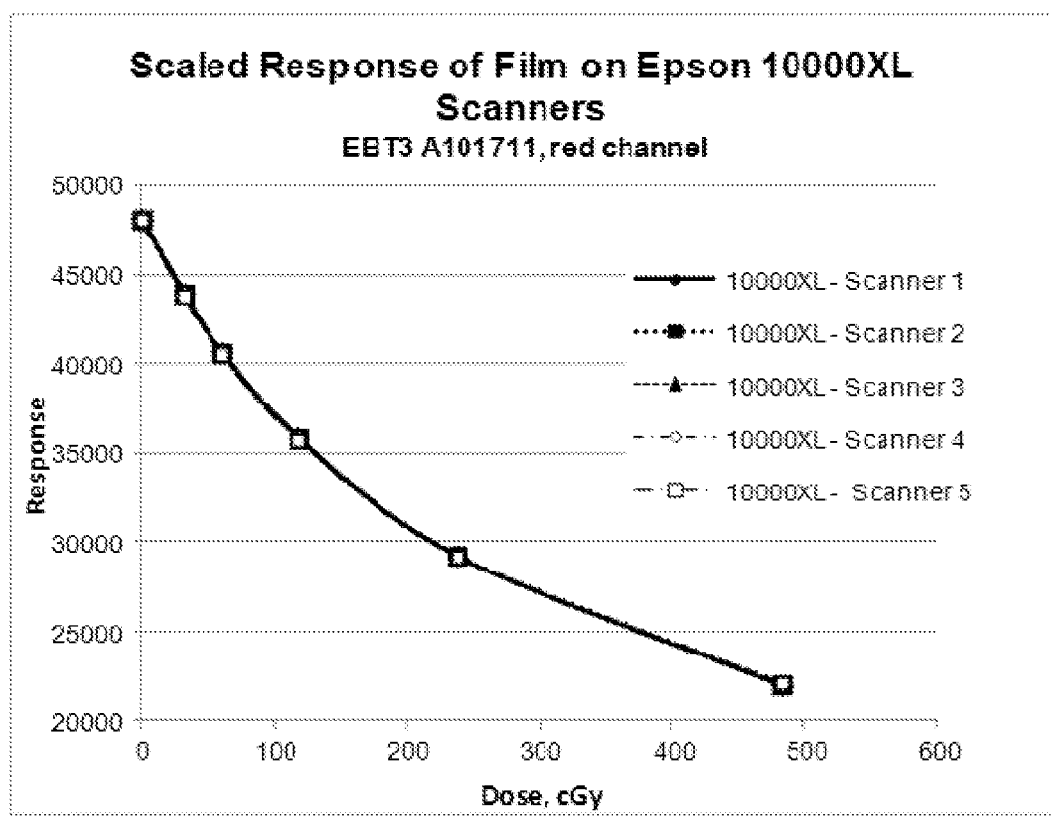
FIG. 5 is a graph of scaled response values plotted against dose values for different scanners of the same type as described in Example 8.

After the images had been scaled the response values of all the films in all the images were measures and plotted against the calibrated exposure dose. The results for the red color channel are displayed in FIG. 5. Note that the images represent different scanners and different times-after-exposure. For Scanner 2 results are shown for two different times-afterexposure. Similar results were obtained from measurements in the green and blue color channels.

The results demonstrate that for the same type of scanner the scanner-to-scanner difference can be compensated for by a using simple scaling process. Thus a number of films from a given production lot would be exposed to known doses. Together with an unexposed film from the same lot, all films would be scanned together at the same time-after-exposure. In practice it would not be necessary that the time-after-exposure be identical for all films, but rather the differences in timing would be small relative to the elapsed time-after-exposure. A function would be applied to fit the dose-response data from the calibration films. Together with the fitted coefficients, this becomes the master calibration function. Given a film from the same production lot from which dose measurements are to be made, two additional films from the same production lot would be required; a piece of unexposed film and a piece of film exposed to a known dose immediately before or after the film to be measured. The three films would be scanned together on any scanner of the same model as the scanner used for calibration at a long time-after-exposure compared to the timing differences between the two exposed films. The digital image would scaled to equalize the response values corresponding to the unexposed film to the response values of the unexposed calibration film in the image from the calibration scanner and then converted to a dose image using the master calibration function. Finally the dose image would be scaled so the dose values correspond to the film exposed to a known dose.

Example 9

This example is included to show that dose-response information obtained from two scanners of different types can be scaled to establish a correspondence in a way similar to that described in the previous Examples.

The film samples described in Examples 6 and 7 were used and were scanned on an Epson 10000XL scanner and three different Epson V700 scanners at different times-after-exposure to acquire 48-bit rgb digital images at a spatial resolution of 72 dpi. The images from all scanners were scaled to equalize the response values of the unexposed films to the value of the unexposed film from the 10000XL scanner. Using the image for the red color channel measurements were made in those areas of the images corresponding to the film exposed to the greatest dose (482.6 cGy). The response values in the image from Scanner X were then scaled based on the response difference between unexposed film and 482.6 cGy exposed film in the image from the 10000XL scanner divided by the similar response differences in the image from Scanner X.

Figure 6:
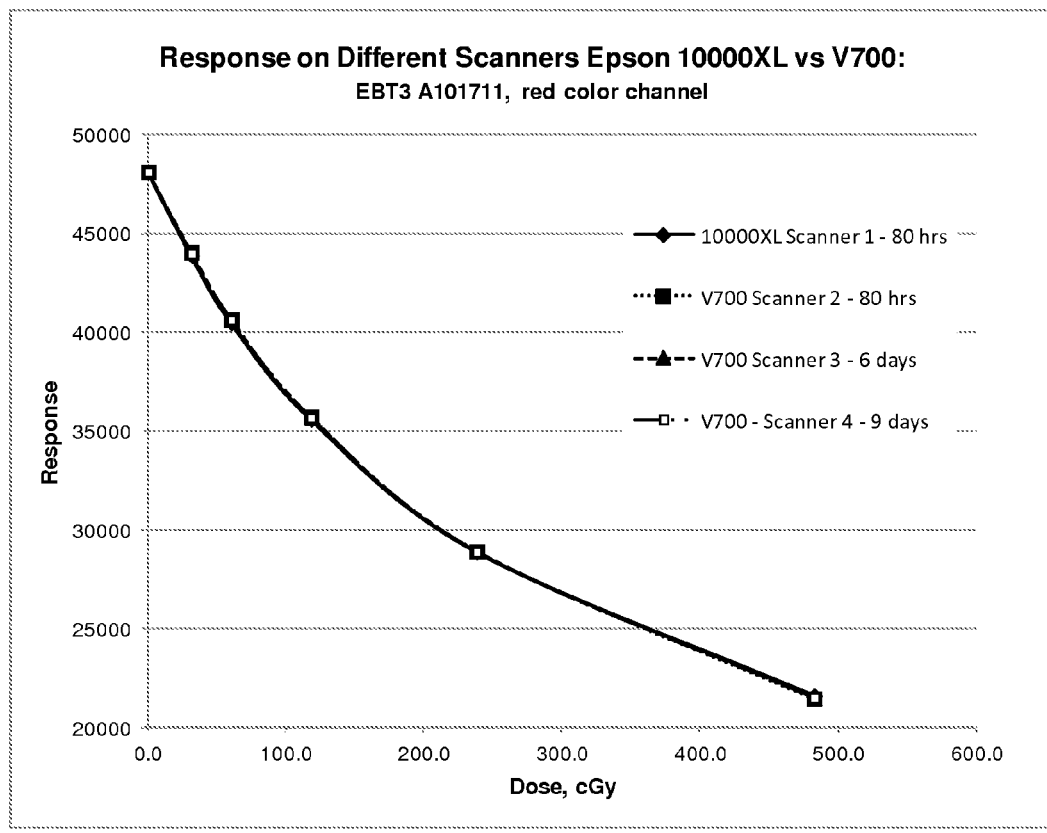
FIG. 6 is a graph of scaled response values plotted against dose values for scanners of different types as described in Example 9.

After the images had been scaled the response values of all the films in all the images were measured and plotted against the calibrated exposure dose. The results for the red color channel are displayed in FIG. 6. Note that the images represent different scanners and different times-after-exposure. Similar results were obtained from measurements in the green and blue color channels.

The results again demonstrate that for different Epson scanner models the scanner-to-scanner difference can be compensated for by a using simple scaling process. Thus a number of films from a given production lot would be exposed to known doses. Together with an unexposed film from the same lot, all films would be scanned together at the same time-after-exposure on an Epson 10000XL or V700 scanner. In practice it would not be necessary that the time-after-exposure be identical for all films, but rather the differences in timing would be small relative to the elapsed time-after-exposure. A function would be applied to fit the dose-response data from the calibration films. Together with the fitted coefficients, this becomes the master calibration function. Given a film from the same production lot from which dose measurements are to be made, two additional films from the same production lot would be required; a piece of unexposed film and a piece of film exposed to a known dose immediately before or after the film to be measured. The three films would be scanned together on any Epson 10000XL or V700 scanner at a long time-after-exposure compared to the timing differences between the two exposed films. The digital image would be scaled to equalize the response values corresponding to the unexposed film to the response values of the unexposed calibration film in the image from the calibration scanner and then converted to a dose image using the master calibration function. Finally the dose image would be scaled so the dose values correspond to the film exposed to a known dose.

Example 10

Figure 7:
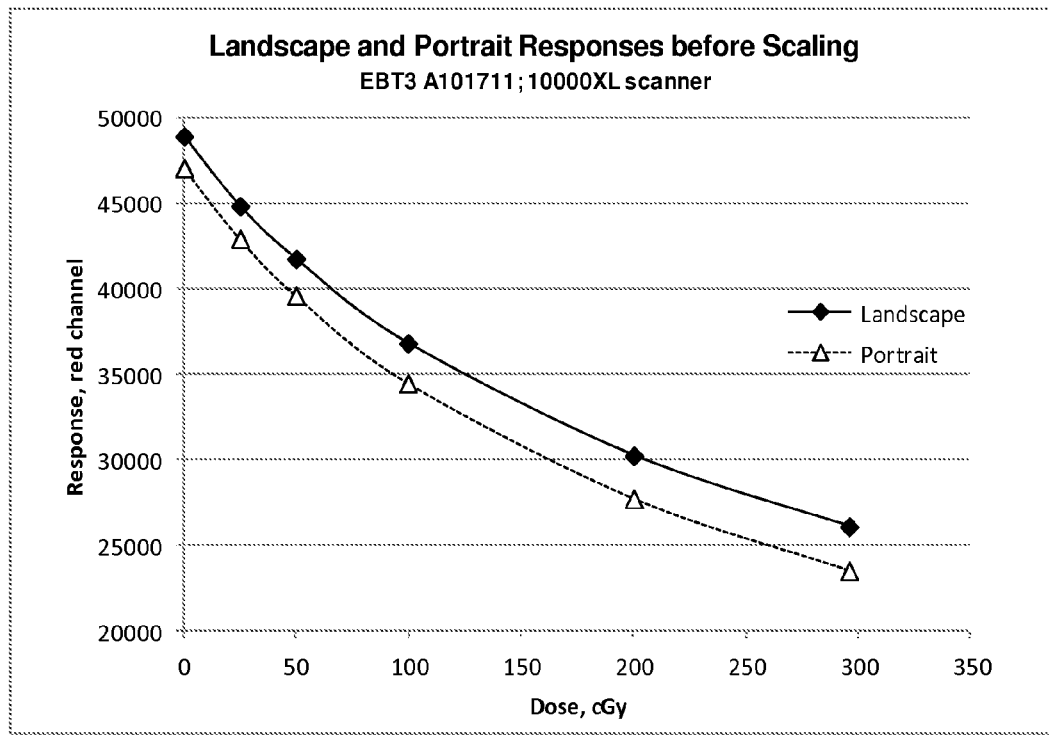
FIG. 7 is a graph of response values plotted against dose values before scaling for landscape and portrait orientations as described in Example 10.

This example is included to demonstrate there is a similarity in the relationship between exposure dose and film response for radiochromic film scanned in different orientation. It is well known that the response of radiochromic film is orientation dependent when digital images are acquired by scanning film on a flatbed scanner. The cause of this is believed to be partly due to anisotropic light scattering by the film and partly due to the polarization of the transmitted light. Portrait orientation refers to the alignment of a rectangular film is placed the longer axis parallel to the scan direction. Conversely the term landscape orientation is used to describe alignment of a rectangular film with the shorter axis parallel to the scan direction. The data shown in FIG. 7 is typical of the dose-response characteristic for Gafchromic EBT3 radiochromic films measured in the red color channel on an Epson 10000XL or V700 rgb flatbed scanner. Dose-response measurements in the green and blue color channels have a similar characteristic. This behavior of Gafchromic EBT3 radiochromic film is similar to EBT2 film.

Figure 8:
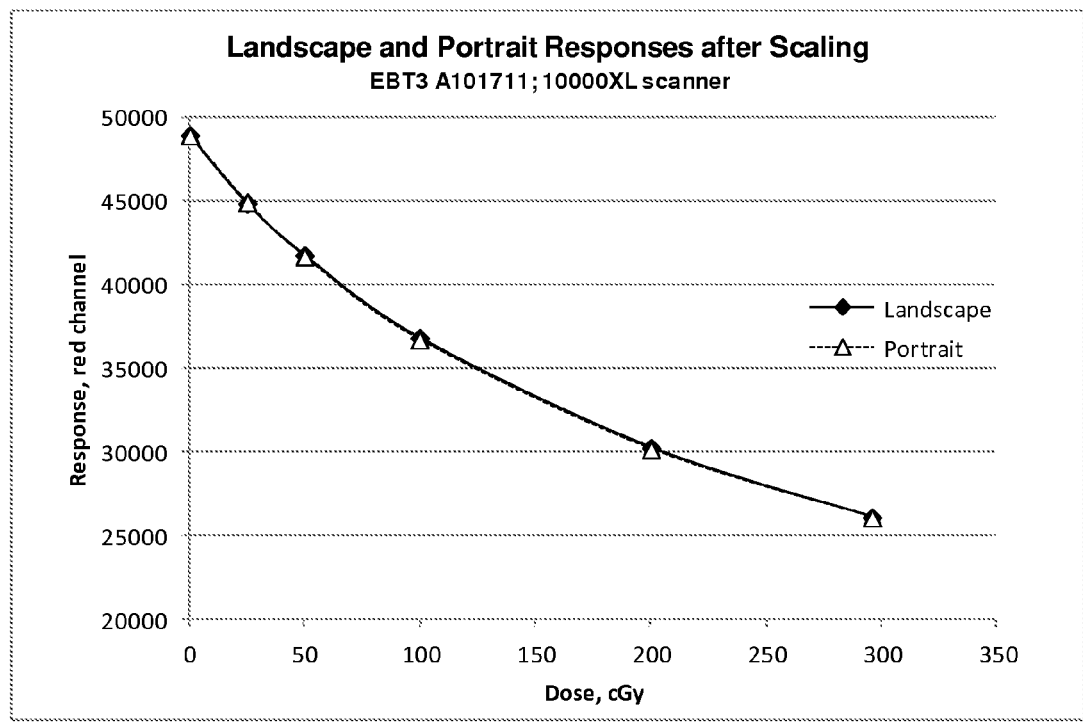
FIG. 8 is a graph of response values plotted against dose values after scaling for landscape and portrait orientations as described in Example 10.

FIG. 8 shows the behavior after the response data is scaled, i.e., the responses of all films are scaled so as to equalize the responses of the unexposed film in the two orientations. Then, in the example, the response of the exposed films scanned in the portrait orientation is scaled in proportion to the net differences between unexposed film and film exposed to 299 cGy in the two orientations. Treated in this way the responses in the two orientations are almost identical. Having obtained a dose-response calibration for one orientation it would be possible to use that calibration for a measurement film scanned in either orientation provided that if the measurement film is scanned in a different orientation two other films having known exposure are also scanned in the different orientation and are used to provide a 2-point scaling of the calibration data or the measurement film.

Example 11

This example is included to demonstrate difference in the response of different production lots of radiochromic film. Samples were obtained from five different lots of Gafchromic EBT3 dosimetry film and exposed to x-rays at doses of approximately 30 cGy, 60 cGy, 120 cGy, 240 cGy and 480 cGy. The exposed films from a production lot together with a sample of unexposed film from the same lot were arranged on an Epson V700 scanner and a 48-bit rgb digital image was acquired at a spatial resolution of 72 dpi. The areas in an image corresponding to the radiochromic film were measured using FilmQA Pro software. The measured responses for each film lot were normalized relative to the response of unexposed film and then scaled to equalize the response differences between the unexposed film and the film exposed to 480 cGy.

Figure 9:
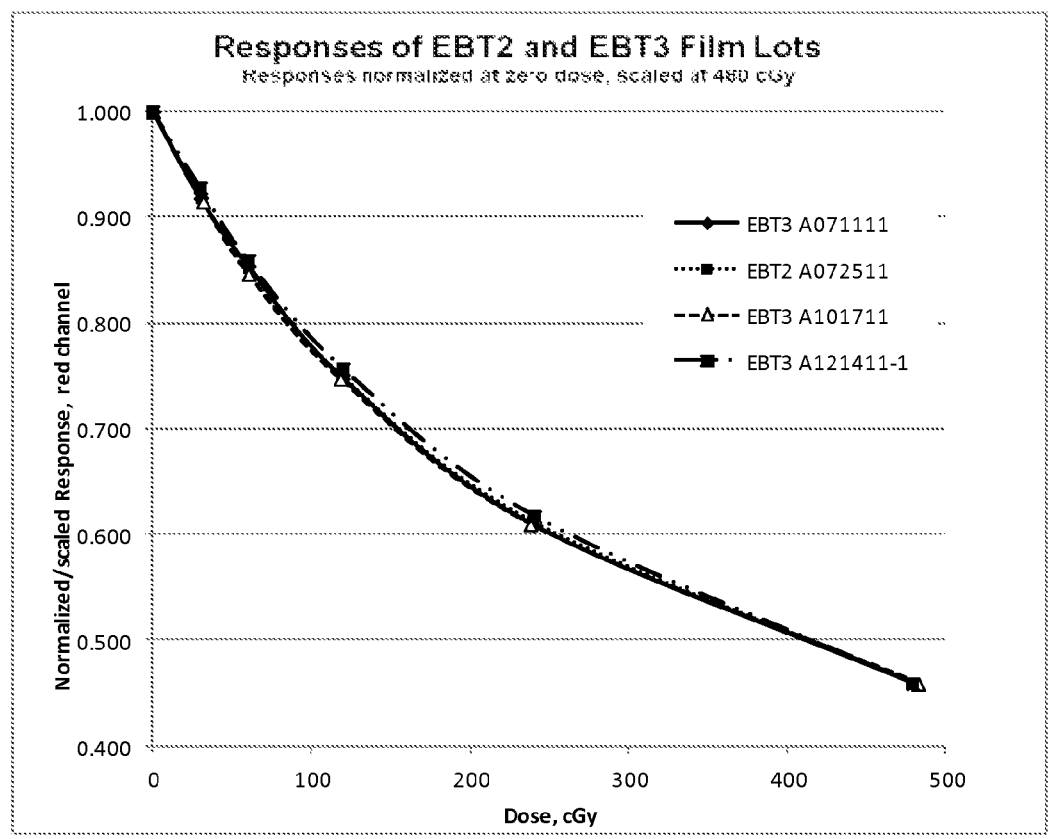
FIG. 9 is a graph of normalized response values plotted against dose values for different production lots of radiochromic film as described in Example 11.

The results plotted in FIG. 9 show that there is a substantial difference between the responses of the production lots. Although there are similarities in the shapes of the response curves it would be unreliable to apply a two-point dose-response calibration for one production lot of radiochromic to any other production lot of the same film type. Similar results are obtained from the measurements made with data from the green and blue color channels.

As a further illustration the following is presented. The digital image of films acquired from production lot A110211 was converted to a dose image using the dose-response calibration information for production lot A101711. Measurements of the dose image at the locations corresponding to the exposed films yielded the values in Table 15. There is a large discrepancy between the measured dose values and the calibrated exposure doses. Then a two-point re-calibration of the data was applied by equalizing the response of the unexposed film in the images and scaling the measured dose for the film with the highest dose to 487.6 cGy, equal to the calibrated exposure dose. Results in Table 16 show better correspondence between the applied and measured doses, but substantial differences remain. Similar results are obtained from the measurements made with data from the green and blue color channels.

TABLE 15

EBT3 Production Lot #A110211

| Calibrated exposure dose, cGy | Measured Using Lot A101711 Calibration |
|---|---|
| 0.0 | 5.7 |
| 31.9 | 31.2 |
| 59.5 | 54.0 |
| 121.6 | 105.2 |
| 242.8 | 208.7 |
| 487.8 | 441.4 |

TABLE 16

EBT3 Production Lot #A110211

| Calibrated exposure dose, cGy | Calibrated with Lot A101711; Measured after 2-point re-calibration |
|---|---|
| 0.0 | 0.4 |
| 31.9 | 27.8 |
| 59.5 | 52.8 |
| 121.6 | 109.2 |
| 242.8 | 224.0 |
| 487.6 | 487.6 |

Example 12

This Example illustrates the advantage of applying a three-point re-calibration to the dose-response data in the digital image. As in Example 11, the digital image acquired from EBT3 film production lot A110211 was used. The areas corresponding to the unexposed film and films exposed to 59.5 cGy and 487.8 cGy were measured and the values used to apply a mathematical correction to the dose-response calibration function for Lot A101711. The calibration function with the three-point re-calibration correction was then applied to convert the digital image of films from lot A110211 to an image in dose space and the doses of all the films were measured. The results in Table 17 show that the measured doses are very close to the calibrated exposure doses and demonstrate that benefit of three-point recalibration. Similar results are obtained from the measurements made with data from the green and blue color channels.

TABLE 17

EBT3 Production Lot #A110211

| Calibrated exposure dose, cGy | Calibrated with Lot A101711; Measured after 3-point re-calibration |
|---|---|
| 0.0 | 0.4 |
| 31.9 | 31.5 |
| 59.5 | 59.5 |
| 121.6 | 121.4 |
| 242.8 | 241.7 |
| 487.8 | 487.8 |

The calibration curve may be generated by relating the radiation dose applied to the film to the measured scanner response. The relationship could be a direct one, where the input image for the software is the raw signal measure of the light transmitted through that region (as with a film scanner) or it could also be preprocessed by applying a correction table or other factor that converts the exposure level to optical density and then the corrected image becomes the input image that is used by the software.

Although the present invention is shown and described with respect to certain aspects, it is obvious that various modifications will become apparent to those skilled in the art upon reading and understanding the specification and the appended claims. The present invention includes all such improvements and modifications and is limited only by the scope of the claims.

What is claimed is:

1. A method for measuring a two-dimensional distribution of ionizing radiation doses with high spatial resolution comprising exposing a radiation sensitive film to a pattern of ionizing radiation that is to be measured to produce a measurement film and exposing one or more radiation sensitive films to known calibrated doses of said ionizing radiation to produce one or more scaling films, simultaneously scanning said measurement film and said scaling film(s) together with an unexposed radiation sensitive film in a multiplicity of measurement channels to produce a digital image, measuring those areas of the digital image corresponding to said unexposed film and said scaling film(s) in said measurement channels, converting said digital image to a map of dose values based on a previously determined mathematical relationship between measured scanner response values for the film in said measurement channels and radiation dose and subsequently adjusting all the dose values corresponding to said digital image using a mathematical function so that the dose values in the areas of said digital image representative of said unexposed film and said scaling films are equal to the calibrated dose values to which they were exposed, wherein all of the radiation sensitive films are the same type of film wherein at least one scaling film is exposed to a radiation dose greater than the highest dose in the measurement film.

2. The method of claim 1 wherein the previously determined mathematical relationship is established by exposing at least one radiation sensitive film to a plurality of known calibrated doses of the ionizing radiation to form a calibration film, scanning said exposed film together with an unexposed radiation sensitive film on an optical scanner having a multiplicity of color measurement channels to produce a calibration digital image, measuring, in a multiplicity of color channels, those areas of the calibration digital image corresponding to the exposed and unexposed film and associating the measured responses in said areas of the calibration digital image to said known ionizing radiation doses to establish the relationship between the measured response values and the ionizing radiation doses, wherein all of the radiation sensitive films are the same type of film.

3. The method of claim 1 wherein the radiation sensitive films are radiochromic films.

4. The method of claim 3 wherein the radiochromic film contains a diacetylene.

5. The method of claim 1 wherein the number of scaling films is one.

6. The method of claim 1 wherein the number of scaling films is two.

7. The method of claim 1 wherein the number of scaling films and calibrated scaling doses is one.

8. The method of claim 1 wherein the number of scaling films and calibrated scaling doses is two.

9. The method of claim 1 wherein the radiation sensitive film has a spatial resolution of at least 1 mm.

10. The method of claim 9 wherein the spatial resolution of the radiation sensitive film is at least 0.1 mm.

11. The method of claim 10 wherein the spatial resolution of the radiation sensitive film is at least 0.01 mm.

12. The method of claim 11 wherein the spatial resolution of the radiation sensitive film is at least 0.001 mm.

* * * * *